United States Patent [19]

Bombardelli et al.

[11] Patent Number: 5,880,160
[45] Date of Patent: Mar. 9, 1999

[54] COLCHICINE DERIVATIVES, THE USE THEREOF AND FORMULATIONS CONTAINING THEM

[75] Inventors: Ezio Bombardelli; Bruno Gabetta, both of Milan, Italy

[73] Assignee: Indena S.p.A., Milan, Italy

[21] Appl. No.: 670,878

[22] Filed: Jun. 27, 1996

[30] Foreign Application Priority Data

Jun. 27, 1995 [IT] Italy ................. MI95 A 1367

[51] Int. Cl.⁶ ................... A61K 31/16; C07C 233/05
[52] U.S. Cl. ................. 514/628; 514/25; 514/623; 514/625; 514/886; 514/538; 514/541; 536/4.1; 564/209; 564/210; 564/211; 564/212; 558/42
[58] Field of Search ............................ 564/209, 210, 564/211, 212, 213; 514/625, 623, 628, 25, 886, 538, 541; 536/4.1

[56] References Cited

U.S. PATENT DOCUMENTS 5,426,224  6/1995  Lee et al. ................. 564/177

OTHER PUBLICATIONS

Capraro et.al., Helv. Chim.Acta, vol. 62, pp. 965–970, 1979.
Brossi, J. Med. Chem., vol. 33, No. 9, pp. 2311–2319, 1990.
Rosner et al. J. Med. Chem., vol. 24, pp. 257–261, 1981.
Quinn et al, J. Med. Chem., vol. 24, pp. 251–256, 1981.
Ringel et al., J. Med. Chem. 34:3334–38 (1991).
Muzaffer et al., J. Med. Chem. 33:567–71 (1990).
Lettre et al., Liebigs Ann. Chem. 758:185–189 (1972).

*Primary Examiner*—Shailendra Kumar
*Attorney, Agent, or Firm*—Pennie & Edmonds LLP

[57] ABSTRACT

The present invention relates to novel colchicine derivatives having antiproliferative, antineoplastic, antiinflammatory and muscle relaxant activities; said derivatives include novel colchine nitrogen amides for use either as such or after derivatization of the hydroxyl at $C_3$ of the aromatic ring and at $C_{10}$ of the tropolone ring. These novel compounds have a cytotoxicity on human tumoral cell lines comparable with colchicine but, in comparison with the latter, they are much more active on cells resistant to the usual antiblastics. The compounds can be included in pharmaceutical formulations useful for the intravenous, oral and topical administrations.

12 Claims, No Drawings

COLCHICINE DERIVATIVES, THE USE THEREOF AND FORMULATIONS CONTAINING THEM

TECHNICAL FIELD

The present invention relates to novel colchicine derivatives having antiproliferative, antineoplastic, antiinflammatory and muscle relaxant activities, the methods for the preparation thereof and the pharmaceutical formulations containing them.

BACKGROUND ARTS

Colchicine is a known pseudo-alkaloid widely used for a very long time in therapy for the treatment of gout, a pathology on which it acts very quickly and specifically, even though it should be used for short times due to its toxicity. A colchicine derivative, namely thiocolchicoside, is widely used to treat contractures and in inflammatory conditions on skeletal muscles. In addition, colchicine is a very potent antiblastic agent, which acts block the formation of the mitotic spindle during cell division; this latter aspect has been investigated thoroughly for any antineoplastic activity and a great deal of colchicine derivatives have been prepared for this purpose. Colchicine as such and a number of its derivatives could not be used clinically due to their high toxicity, and therefore their unacceptable risk/benefit ratio. Only one colchicine derivative, demecolcine, is used in some degree in oncology for the treatment of certain leukemia forms. It would thus be desirable to have compounds which possess higher activity, lower toxicity and higher therapeutical index. More specifically, in the antineoplastic field, researches have been focused on the search for products having, besides a normal cytotoxicity, a cytotoxicity aimed at cell lines resistant to the known, usual antiblastic medicaments.

SUMMARY OF THE INVENTION

The derivatives of the present invention have the formula I:

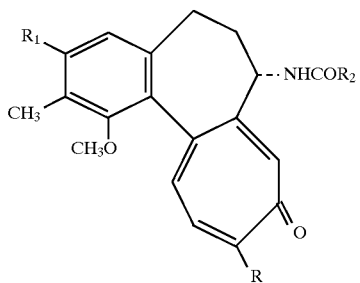

wherein R is a methoxyl or thiomethyl group; $R_1$ is hydroxy; a B-D-glucopyranosyloxy residue; a B-D-glucopyranosyloxy residue ketalized at the hydroxyls 4' and 6' with an aliphatic or aromatic aldehyde; a 6-deoxygalactopyranosyloxy residue; an acyloxy group of $C_{16}$ to $C_{22}$ polyunsaturated fatty acids; straight, branched or cyclic O-alkyl $C_1$–$C_6$, saturated or unsaturated; and $R_2$ is a $C_1$–$C_6$ haloalkyl group.

Particularly preferred compounds of formula I are those in which $R_1$ is a methoxy group, a B-D-glucopyranyloxy residue optionally ketalized at the 4' and 6' hydroxyls with an aromatic or aliphatic aldehydes, for example, 2- or 3-thienal or a ximenoyloxy group.

$R_2$ is preferably trifluoromethyl, pentafluoroethyl or heptafluoropropyl.

DETAILED DESCRIPTION OF THE PREFERRED EMBODIMENTS

Compounds I are prepared starting from the natural compounds colchicine or thiocolchicine (Formula I, $R_1$=—$OCH_3$, $R_2$=$CH_3$, R=—$OCH_3$ or —$SCH_3$, respectively) or from the corresponding derivatives thereof glucosylated at the hydroxyl at the 3- position or also from the N-formyl-N-deacetyl-derivatives thereof.

The hydrolysis of these natural compounds with aqueous solutions of strong mineral acids makes it possible to obtain selectively, changing the temperature and the reaction time, the corresponding N-deacetyl and 3-demethyl-N-deacetyl derivatives which can then be subjected to conventional reactions of N-acylation and alkylation or acylation at the hydroxyl at the 3-position.

In the case of thiocolchicine, the hydrolysis with hydrohalogen acids or, more preferably, with sulfuric acid (20% $H_2SO_4$—120 h) allows one to obtain N-deacetylthiocolchicine and 3-demethyl-N-deacetylthiocolchicine in essentially quantitative yields.

The compounds of the invention have a remarkable antitumour activity.

The table shows the antimitotic activity of the compounds of the invention on a cultured breast tumour explant, compared with colchicine and Taxol.

TABLE

In vitro cytotoxic activity of some thiocolchicine derivatives.

| | $IC_{50}$ (nM) | | |
|---|---|---|---|
| Compounds | MCF7-ADR (resistant) | MCF-7 (human breast) | MCF7-ADR/MCF7 |
| Colchicine | 112 ± 4.2 | 4.4 ± 0.3 | 25.45 |
| Compound I | 26 ± 2.3 | 6.2 ± 0.4 | 4.2 |
| Compound II | 11 ± 1.9 | 5.0 ± 0.2 | 2.2 |
| Compound III | 7 ± 0.4 | 4.1 ± 0.3 | 1.7 |
| Compound IV | 31 ± 1.9 | 3.2 ± 0.2 | 9.7 |
| Taxol | 360 ± 7.8 | 6.1 ± 0.3 | 59.01 |

This table evidences that the compound of the invention have significant advantages on the resistant cell lines, which are nowadays considered the main target for cytotoxic medicaments.

Moreover, the products according to the present invention have antiinflammatory and muscle relaxant activities and they can be incorporated in pharmaceutical formulations useful for the administration of the medicament for the indicated pathology. Formulations for the intravenous, oral, transdermal, epicutaneous administrations can conveniently be prepared. Such formulations are generally known to one of ordinary skill in the art and need not be described in great detail here.

Among the excipients useful to prepare said formulations, natural and synthetic phospholipids proved to be particularly useful for preparing liposomial forms for the parenteral, intravenous and/or topical routes. The same formulations proved to be useful in the topical treatment of cutaneous epitheliomas and in cutaneous hyperproliferative conditions, such as psoriasis. In the specific antineoplastic field, besides the phospholipids which allow the administration of the medicament in the liposomial form, some surfactants such as polyethoxylated castor oils, or polysorbates acting synergistically with the active ingredient, turned out to be particularly useful. Preferably the active principle is micronized until the compound is dissolved in water. In oncology, the products are used at dosages from 1 to 100 mg/m$^2$.

EXAMPLES

The following examples further illustrate the invention.

Example I

Preparation of N-deacetyl-N-pentafluoro-propionyl-thiocolchicine. (Compound I; R=—SCH$_3$ R$_1$=—OCH$_3$ R$_2$=—CF$_2$—CF$_3$)

20 g of thiocolchicine are dissolved in 300 ml of 20% sulfuric acid and heated under nitrogen atmosphere for 36 h at 100° C.; the reaction mixture is alkalinized to pH 8 to separate 15 g of N-deacetyl-thiocolchicine.

This product is dissolved in acetone and, in the presence of anhydrous Na$_2$CO$_3$, it is reacted with 1.5 equivalents of perfluoropropionic anhydride under strong stirring; after 2 h the reaction mixture is filtered and the solvent is evaporated off. The oily residue is taken up with methanol, from which N-deacetyl-N-pentafluoropropionylthiocolchicine is separated by crystallization.

Example II

Preparation of N-deacetyl-N-pentafluoropropionyl-3-O-ximenoyl-thiocolchicine. (Compound II; R=—SCH$_3$ R$_1$=—O-Ximenoyl R$_2$=—CF$_2$—CF$_3$)

20 g of thiocolchicoside are dissolved in 300 ml of 20% sulfuric acid and the whole is heated under nitrogen atmosphere 36 h at 100° C.; from the reaction mixture 12 g of N-deacetyl-3-O-demethylthiocolchicine separate.

This product is dissolved in acetone and, in the presence of anhydrous Na$_2$CO$_3$, is reacted with 3 equivalents of perfluoropropionic anhydride under strong stirring; after 2h the reaction mixture is filtered and the solvent and the reactive excess are removed under vacuum. The residue consisting of N-deacetyl-N-pentafluoropropionyl-3-O-demethyl-3-O-pentafluoropropionate is taken up with methanol containing NH$_4$Cl, checking the hydrolysis of the phenol ester by thin layer chromatography (toluene/ethyl acetate 1:1); the solvent is evaporated to dryness under vacuum and the residue is dissolved in acetone, filtering off the insolubles. The acetone solution is concentrated to dryness and the residue is taken up with 100 ml of pyridine; this solution is cooled at 0° C. and added with 2 eq. of ximeninic acid chloride under strong stirring. The reaction mixture is left to stand overnight and then poured onto 500 g of ice. The formed aqueous suspension is extracted for three times with 500 ml of methylene chloride. The organic phase is washed with water, then with a hydrochloric acid diluted solution and again with water. The phase organic is dried over Na$_2$SO$_4$ and concentrated to dryness. The residue is crystallized from an ethyl acetate/isopropyl ether mixture, to obtain 27 g of N-deacetyl-N-pentafluoropropionyl-3-O-ximenoyl-thiocolchicine.

Example III

Preparation of N-deacetyl-N-pentafluoropropionyl- 3-O-demethyl-3-O-cyclopentenyl-thiocolchicine. (Compound III; R=—SCH$_3$ R$_1$=—O-cyclopentenyl R$_2$=—CF$_2$—CF$_3$)

20 g of thiocolchicoside are dissolved in 300 ml of 20% sulfuric acid and the mixture is heated under nitrogen atmosphere for 36 h at 100° C.; 12 g of N-deacetyl-3-O-demethylthiocolchicine separate from the reaction mixture.

This product is dissolved in acetone in the presence of anhydrous Na$_2$CO$_3$ and reacted with 3 equivalents of pentafluoropropionic anhydride under strong stirring; after 2 h the reaction mixture is filtered and the solvent and reactive excess are removed under vacuum. The residue consisting of N-deacetyl-N-pentafluoro-propionyl-3-O-demethyl-3-O-pentafluoropropionate is taken up with methanol containing NH$_4$Cl, checking the hydrolysis of the phenol ester by thin layer chromatography (toluene/ethyl acetate 1:1); the solvent is evaporated to dryness under vacuum and the residue is dissolved in acetone filtering off the insolubles. The acetone solution is added with Na$_2$CO$_3$ and 5 equivalents of cyclopentenyl bromide with respect to starting product. The reaction is stirred for 6 h checking the alkylation by thin layer chromatography. When the reaction is complete, salts are filtered off and the solvent is distilled under vacuum. The residue is chromatographed on a silica gel column using ethyl acetate as eluent. The fractions containing the desired product are collected, solvent is removed and the product is crystallized from acetone/hexane. 9.2 g of N-deacetyl-N-pentafluoropropionyl-3-O-cyclopentenyl-thiocolchicine are obtained.

Example IV

Preparation of N-deacetyl-N-heptafluorobutyroyl-thiocolchicine. (Compound IV; R=—SCH$_3$ R$_1$=—OCH$_3$ R$_2$=—CF$_2$—CF$_2$—CF$_3$)

10 g of N-deacetylthiocolchicine are dissolved in 150 ml of anhydrous acetone in the presence of Na$_2$CO$_3$ and treated at room temperature with 1.5 eq. of heptafluorobutyroyl anhydride. Na$_2$CO$_3$ and the solvent are removed and the residue is purified with isopropyl ether to give 12.5 g of N-deacetyl-heptafluoro-butyroylthiocolchicine.

Example V

Preparation of N-deacetyl-N-pentafluoropropionyl-3-O-isopropyl-thiocolchicine. (R=—SCH$_3$ R$_1$=—O-isopropyl R$_2$=—CF$_2$—CF$_3$)

For the preparation of this derivative, the procedures of example III are repeated, using isopropyl bromide as the reagent. After purification of the crude reaction product on silica gel and crystallization, 7.6 g of N-deacetyl-N-pentafluoropropionyl-3-O-isopropyl-thiocolchicine are obtained, having spectroscopic characteristics in agreement with the desired molecule.

Examples VI, VII and VIII illustrate typical pharmaceutical formulations of the derivatives of the invention

| Example VI - Preparation of tablets containing compound (I): | |
|---|---|
| Compound I | 20 mg |
| Lactose | 47 mg |
| Microcrystalline cellulose | 20 mg |
| Crosslinked carboxymethylcellulose sodium | 5 mg |
| Colloidal silica | 1 mg |
| Talc | 1 mg |
| Magnesium stearte | 1 mg |
| Example VII - Preparation of a liposome cream containing compound (II): | |
| Compound II | 0.2 g |
| Phosphatidylcholine | 20 g |
| Cholesterol | 0.5 g |
| Butylhydroxytoluene | 0.01 g |
| Ethanol 95% | 8 g |
| Disodium edetate | 0.15 g |
| Imidazolidinyl urea | 0.3 g |
| Sodium dehydroacetate | 0.2 g |
| Hydroxyethylcellulose (Natrosol 250 HHX-Aqualon) | 2 g |
| Distilled water | 67.75 g |

-continued

Example VI - Preparation of tablets containing compound (I):

Example VIII - Preparation of an injectable solution containing compound (IV):

| | |
|---|---|
| Compound IV | 50 mg |
| PEG-660 12-hydroxystearate | 2,500 mg |
| Propylene glycole | 1,000 mg |
| Alcohol q.s. | 5 ml |

These formulations are prepared in a conventional manner which is within the abilities of the skilled artisan. These formulations can conveniently be administered to a subject orally (Example VI), topically (Example VII) or by injection (Example VIII) to achieve the beneficial advantages described previously.

What is claimed is:

1. Compounds of formula I

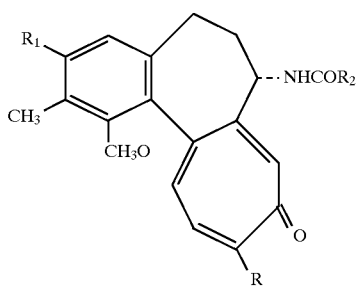

(I)

wherein R is a thiomethyl group;

$R_1$ is hydroxy; a B-D-glucopyranosyloxy residue;

a B-D-glucopyranosyloxy residue ketalized at the 4' and 6' hydroxyls with aliphatic or aromatic aldehydes;

a 6-deoxy-galactopyranosyloxy residue;

an acyloxy group of $C_{16}$ to $C_{22}$ polyunsaturated fatty acids;

straight, branched or cyclic O-alkyl $C_1$–$C_6$, saturated or unsaturated; and

R2 is a $C_1$–$C_6$ haloalkyl group, with the proviso that, when $R_2$ is a $C_1$-haloalkyl group, $R_1$ is not A hydroxy or a methoxy group.

2. Compounds according to claim 1, wherein $R_1$ is a methoxy group, a B-D-glucopyranyloxy residue optionally ketalized at the 4' and 6' hydroxyls with 2- or 3-thienal or a ximenoyloxy group.

3. Compounds according to claim 1 specitrially as:

N-deacetyl-N-pentafluoro-propionyl-thiocolchicine;

N-deacetyl-N-pentafluoro-propionyl-3-O-ximenoyl-thiocolchicine;

N-deacetyl-N-pentafluoropropionyl-3-O-demethyl-3-O-cyclopentenyl-thiocolchicine;

N-deacetyl-N-heptafluoro-butyroyl-thiocolchicine;

N-deacetyl-N-pentafluoropropionyl-3-O-isopropyl-thiocolchicine.

4. Pharmaceutical compositions containing as the active ingredient a compound of claim 1 in admixture with a pharmaceutically acceptable carrier.

5. Compositions according to claim 4, wherein the active ingredient is formulated in aliposome.

6. Compositions according to claim 4, wherein the carrier includes a surfactant of a polyethoxylated castor oil or a polysorbate.

7. A method for the treatment of inflammation of skeletal muscles in a subject which comprises administering to such subject a colchicine derivative according to claim 1 in an amount which is therapeutically effective to reduce such inflammation.

8. A method for causing muscle relaxation in a subject which comprises administering to such subject a colchicine derivative according to claim 1 in an amount which is therapeutically effective to cause muscle relaxation in said subject.

9. A method for blocking the formation of mitotic spindles during cell division in a subject which comprises administering to such subject a colchicine derivative according to claim 1 in an amount which is therapeutically effective to block such formation and thus reduce cell proliferation.

10. The method of claim 7 in which said colchicine derivative is N-deacetyl-N-pentafluoro-propionyl-thiocolchicine; N-deacetyl-N-pentafluoro-propionyl-3-O-ximenoyl-thiocolchicine; N-deacetyl-N-pentafluoro-propionyl-3-O-demethyl-3-O-cyclopentenyl-thiocolchicine; N-deacetyl-N-heptafluoro-butyrol-thiocolchicine; or N-deacetyl-N-pentafluoro-propionyl-3-O-isopropyl-thiocolchicine.

11. The method of claim 8 in which said colchicine derivative is N-deacetyl-N-pentafluoro-propionyl-thiocolchicine; N-deacetyl-N-pentafluoro-propionyl-3-O-ximenoyl-thiocolchicine; N-deacetyl-N-pentafluoro-propionyl-3-O-demethyl-3-O-cyclopentenyl-thiocolchicine; N-deacetyl-N-heptafluoro-butyrol-thiocolchicine; or N-deacetyl-N-pentafluoro-propionyl-3-O-isopropyl-thiocolchicine.

12. The method of claim 9 in which said colchicine derivative is N-deacetyl-N-pentafluoro-propionyl-thiocolchicine; N-deacetyl-N-pentafluoro-propibnyl-3-O-ximenoyl-thiocolchicine; N-deacetyl-N-pentafluoro-propionyl-3-O-demethyl-3-O-cyclopentenyl-thiocolchicine; N-deacetyl-N-heptafluoro-butyrol-thiocolchicine; or N-deacetyl-N-pentafluoro-propionyl-3-O-isopropyl-thiocolchicine.

* * * * *

UNITED STATES PATENT AND TRADEMARK OFFICE
CERTIFICATE OF CORRECTION

PATENT NO. : 5,880,160
DATED : March 9, 1999
INVENTOR(S) : Ezio Bombardelli et al.

It is certified that error appears in the above-identified patent and that said Letters Patent is hereby corrected as shown below:

Column 5, lines 20-31 (claim 1, formula I), change formula I to the following:

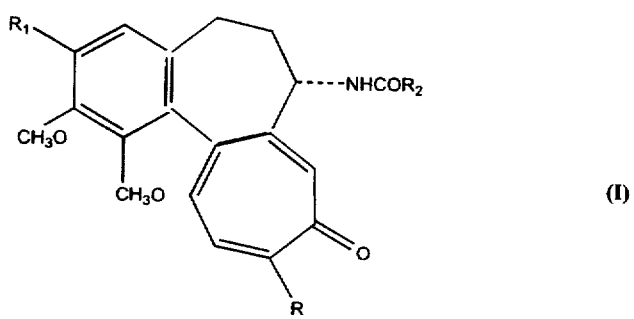

(I)

Column 5, line 41 (claim 1, line 23): change "R2" to --$R_2$--.

Column 5, line 42 (claim 1, line 24): change "A" to --a--.

Column 5, line 48 (claim 3, line 1): change "specitrially" to --specifically--.

Column 6, line 1: after "-thiocolchicine;" insert --or--.

UNITED STATES PATENT AND TRADEMARK OFFICE
CERTIFICATE OF CORRECTION

PATENT NO. : 5,880,160
DATED : March 9, 1999
INVENTOR(S) : Ezio Bombardelli et al.

It is certified that error appears in the above-identified patent and that said Letters Patent is hereby corrected as shown below:

Column 6, line 8 (claim 5, line 2): change "aliposome" to --a liposome--.

Column 6, line 47 (claim 12, line 3): change "propibnyl" to --propionyl--.

Signed and Sealed this

Thirteenth Day of July, 1999

Attest:

Q. TODD DICKINSON

Attesting Officer

Acting Commissioner of Patents and Trademarks